(12) United States Patent
Duncan

(10) Patent No.: US 9,408,614 B2
(45) Date of Patent: Aug. 9, 2016

(54) OLECRANON FRACTURE FIXATION SYSTEM

(75) Inventor: Scott F. M. Duncan, Owatonna, MN (US)

(73) Assignee: MAYO Foundation for Medical Education and Research, Rochester, MN (US)

(*) Notice: Subject to any disclaimer, the term of this patent is extended or adjusted under 35 U.S.C. 154(b) by 1284 days.

(21) Appl. No.: 12/399,400

(22) Filed: Mar. 6, 2009

(65) Prior Publication Data

US 2009/0228009 A1 Sep. 10, 2009

Related U.S. Application Data

(60) Provisional application No. 61/035,274, filed on Mar. 10, 2008.

(51) Int. Cl.
| | |
|---|---|
| *A61B 17/72* | (2006.01) |
| *A61B 17/17* | (2006.01) |
| *A61B 17/88* | (2006.01) |

(52) U.S. Cl.
CPC ......... *A61B 17/1725* (2013.01); *A61B 17/1739* (2013.01); *A61B 17/7225* (2013.01); *A61B 17/7241* (2013.01); *A61B 17/8869* (2013.01)

(58) Field of Classification Search
CPC ........................................ A61B 17/72–17/748
USPC ...................... 606/62–68, 246–279
See application file for complete search history.

(56) References Cited

U.S. PATENT DOCUMENTS

| | | | |
|---|---|---|---|
| 3,990,438 A | 11/1976 | Pritchard | |
| 4,212,294 A | 7/1980 | Murphy | |
| 4,262,665 A | 4/1981 | Roalstad et al. | |
| 4,590,930 A | 5/1986 | Kurth et al. | |
| 4,632,101 A * | 12/1986 | Freedland | ....................... 606/68 |

(Continued)

FOREIGN PATENT DOCUMENTS

| | | |
|---|---|---|
| EP | 0517435 A1 | 9/1992 |
| EP | 1792578 | 6/2007 |

(Continued)

OTHER PUBLICATIONS http://www.acumed.net/product-detail-print.php?productID=18.

(Continued)

*Primary Examiner* — Nicholas Plionis
(74) *Attorney, Agent, or Firm* — Quarles & Brady, LLP

(57) ABSTRACT

An olecranon fracture fixation system includes an intramedullary core that is dimensioned for insertion in an intramedullary canal of the bone, and a hollow shell that is dimensioned for insertion in the intramedullary canal. The shell includes fixation elements that extend outwardly away from a proximal end of the shell. A fastener is provided for attaching the shell to the core in the intramedullary canal. When the core and shell are inserted in the intramedullary canal, the fixation elements extend away from the fracture line of the bone, and when the core and shell are attached in the intramedullary canal, the fixation elements engage an end surface of the end section of the bone. In one example version of the invention, the system is an olecranon fracture fixation system wherein the fixation elements are dimensioned to engage the triceps tendon and an end surface of the olecranon when the core and shell are attached in the intramedullary canal of the proximal ulna.

19 Claims, 3 Drawing Sheets

(56) References Cited

U.S. PATENT DOCUMENTS

| | | | |
|---|---|---|---|
| 5,057,103 | A | 10/1991 | Davis |
| 5,549,609 | A | 8/1996 | Frankel et al. |
| 5,779,705 | A | 7/1998 | Matthews |
| 5,810,820 | A | 9/1998 | Santori et al. |
| 6,168,595 | B1 * | 1/2001 | Durham et al. ............... 606/64 |
| 6,558,388 | B1 | 5/2003 | Bartsch et al. |
| 7,037,308 | B2 * | 5/2006 | Medoff ............... 606/319 |
| 2002/0133156 | A1 * | 9/2002 | Cole ............... 606/62 |
| 2002/0151897 | A1 * | 10/2002 | Zirkle, Jr. ............... 606/62 |
| 2007/0270848 | A1 * | 11/2007 | Lin ............... 606/65 |
| 2007/0276382 | A1 * | 11/2007 | Mikhail et al. ............... 606/62 |
| 2008/0177334 | A1 * | 7/2008 | Stinnette ............... 606/304 |
| 2008/0306479 | A1 * | 12/2008 | Bernstein ............... 606/60 |

FOREIGN PATENT DOCUMENTS

| | | | |
|---|---|---|---|
| WO | | 03068080 | 8/2003 |
| WO | WO 2006090226 | A1 * | 8/2006 |

OTHER PUBLICATIONS

Hutchinson et al., Cyclic Loading of Olecranon Fracture Fixation Constructs. J Bone Joint Surg Am. 2003; 85:831-837.

Dieterich et al., The Olecranon Sled—A New Device for Fixation of Fractures of the Olecranon. Acta Orthopaedica 2006; 77 (3): 440-444.

* cited by examiner

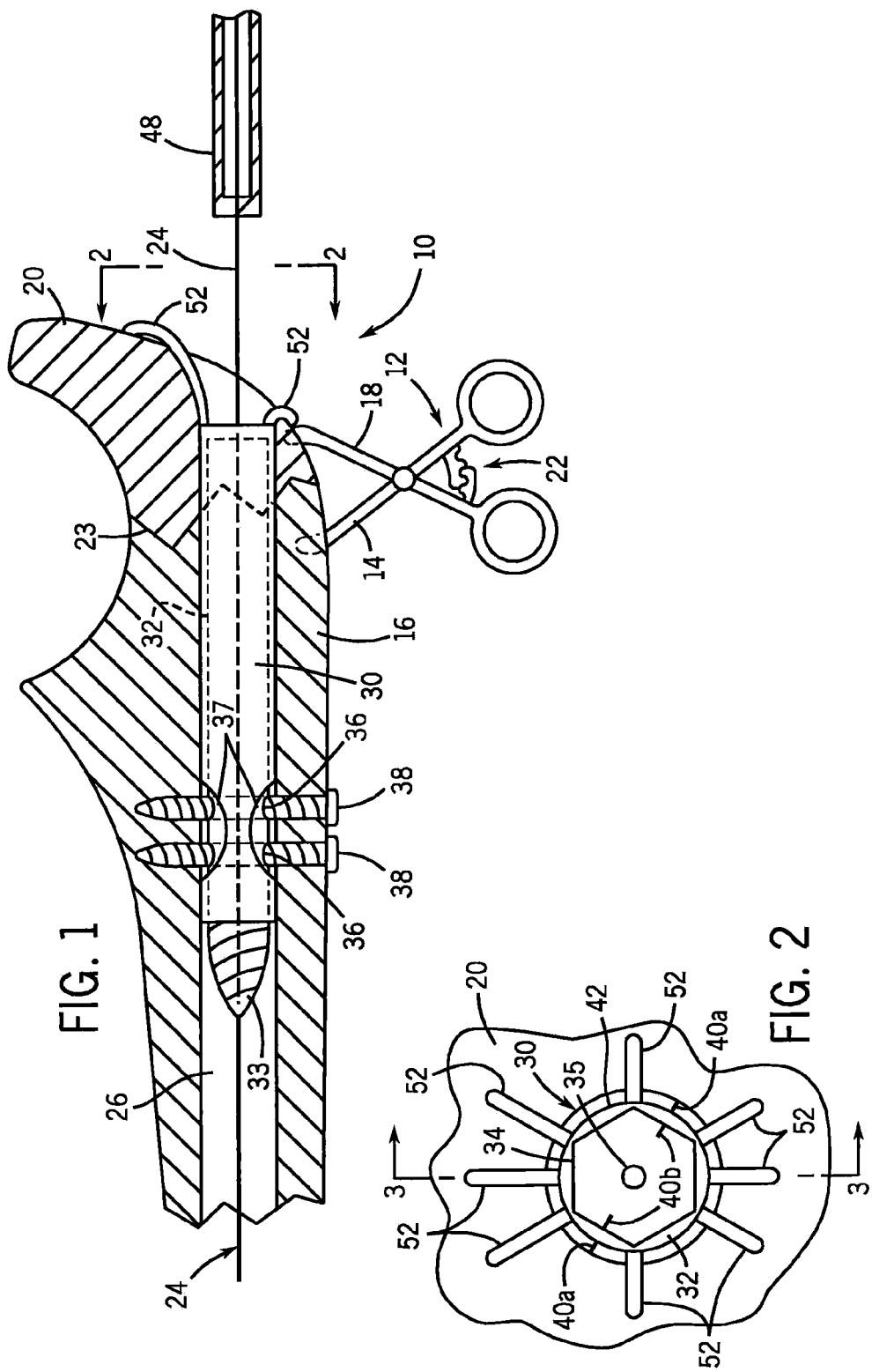

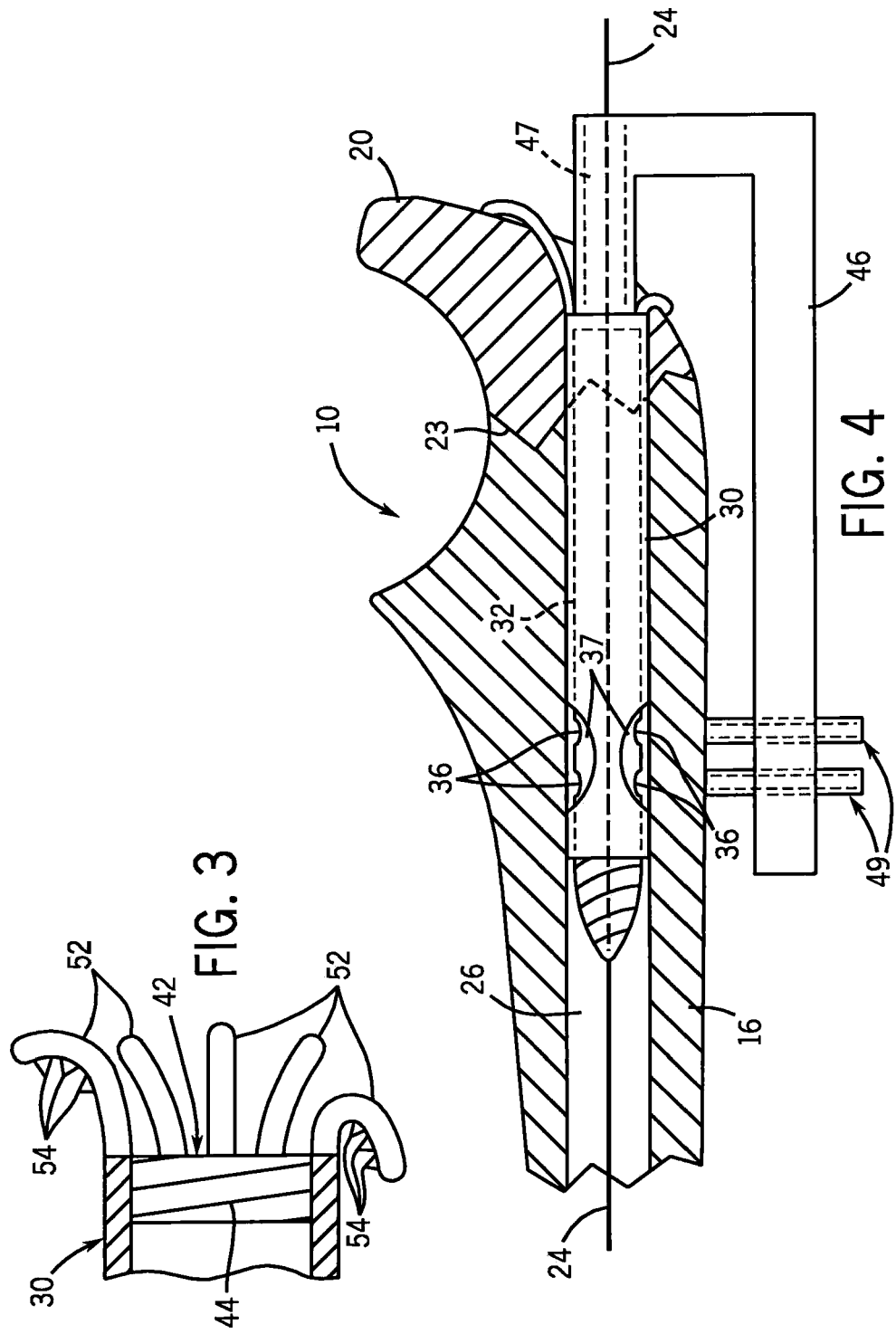

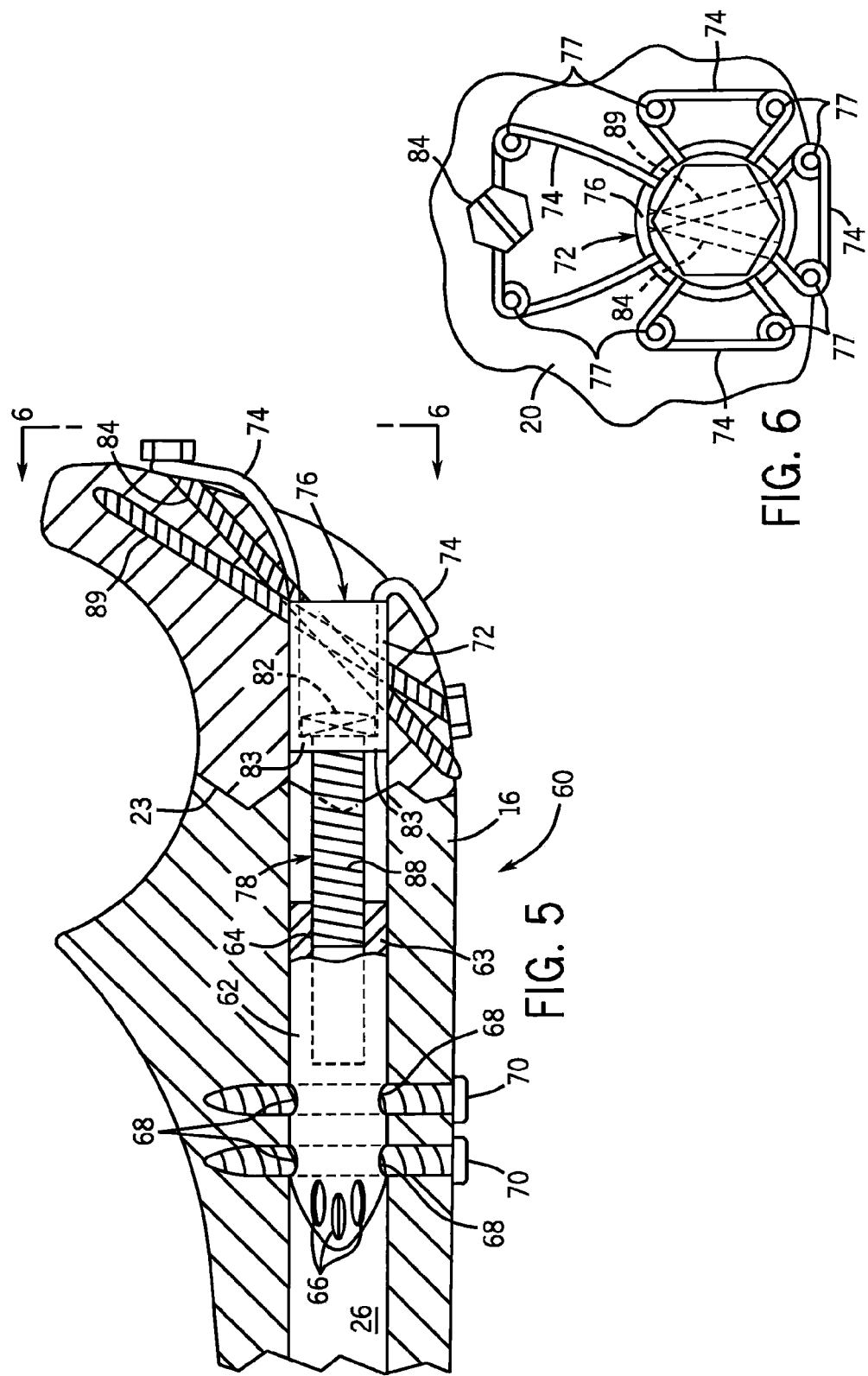

US 9,408,614 B2

OLECRANON FRACTURE FIXATION SYSTEM

CROSS-REFERENCES TO RELATED APPLICATIONS

This application claims priority from U.S. Provisional Patent Application No. 61/035,274 filed Mar. 10, 2008.

STATEMENT REGARDING FEDERALLY SPONSORED RESEARCH

Not Applicable.

BACKGROUND OF THE INVENTION

1. Field of the Invention

The invention relates to devices for the surgical fixation of a fracture to promote bone healing, and more particularly to olecranon fracture fixation systems.

2. Description of the Related Art

The elbow joint includes three bones: the humerus, the ulna, and the radius. These three bones are connected by ligaments, and muscles and tendons move the three bones around each other. During motion, bending and straightening of the elbow occurs between the humerus and the ulna. The olecranon is the part of the ulna that interfaces with the end of the humerus and moves around the end of the humerus to create the hinge-like motion of the elbow. The olecranon is attached by a tendon to the upper arm triceps brachii muscle which straightens the elbow by a pulling force on the olecranon.

Olecranon fractures are quite common, and can impair the ability to straighten the elbow joint. When the olecranon is fractured, the powerful triceps brachii muscle tends to pull the bone fragment upward away from the main portion of the ulna, and it can be difficult to set the bone fragment of the olecranon in its proper position for healing. Therefore, various devices have been developed for fixing bone fragments of the olecranon under compression to enhance the rate of healing.

In a one type of device and associated methods for fixing the olecranon, a hole is drilled in the end of the bone fragment and a cancellous intramedullary screw is directed into the intramedullary canal of the proximal portion of the ulna. Intramedullary screw technology typically uses a 6.5 to 7.3 millimeter screw, and the head of the screw or a washer compresses the olecranon fragment against the proximal ulna. Because the intramedullary screw does not have a locking mechanism, it is at potential risk for backing out, which would result in loss of fixation and need for hardware removal and potential re-operation for repeat fixation.

In another type of device and associated methods for fixing the olecranon, a fixation plate is used. For example, the Mayo Clinic Congruent Elbow Plate System is commercially available from Acumed, Hillsboro Oreg., USA. This plate system is an olecranon plate capable of treating osteotomies and fractures, providing excellent fixation in the proximal ulna. Prongs on the proximal tip of the olecranon plate provide provisional fixation into the triceps tendon, assisting with reduction, and improving final stability. The plate is placed directly over the triceps tendon. Locking screws are interlocked to provide a stable fixed angle structure inside the bone fragment. The plate is applied with compression across the olecranon fracture.

In yet another type of device and associated methods for fixing the olecranon, tension band wiring is used. This technique is shown in FIGS. 1 and 2 of U.S. Pat. No. 7,037,308. Pins are driven longitudinally into the olecranon across the fracture line, and a flexible wire is passed through a drill hole on the ulnar side of the fracture line. The two ends of the wire are crossed over the fracture line to the olecranon side of the fracture line. One wire is then passed under ends of the two pins, and the wire twisted and tightened to the other end of the wire to develop tension in the wire to produce compression across the olecranon fracture. However, tension band wiring has been shown in biomechanical studies to not provide the same strength and rigidity as an intramedullary screw. It also has the problem of backing out and potentially necessitating a second surgery for hardware removal.

In still another type of device and associated methods for fixing the olecranon, there is provided an implant with a wire element having two spaced adjacent legs which are adapted to be implanted longitudinally in the bone across the fracture site. The wire element extends outwardly of the bone, and the legs are bent and extend backwardly into juxtaposition with the legs in the bone and are joined by a U-shaped loop connecting portion. A tensioning device is engageable with the connecting portion and with a fixation device secured to the bone to apply force to the connection portion and produce tension in the wire element to develop compression across the fracture site. See U.S. Pat. No. 7,037,308 and PCT International Publication Number WO 03/068080. One disadvantage with this device is that the U-shaped loop that goes on the outside of the bone and the tensioning device leave hardware prominent on the subcutaneous border of the ulna which can cause patient discomfort.

Still other types of devices and associated methods for fixing the olecranon can be found in U.S. Pat. Nos. 3,990,438, 4,212,294 and 5,549,609 and European Patent Application EP 1792578 A1.

While these known olecranon fracture fixation systems and methods may be acceptable for certain applications, there still exists a need for an improved device for olecranon fracture fixation.

SUMMARY OF THE INVENTION

The present invention addresses the foregoing needs by providing a fracture fixation system for a bone having a fracture line between a central section of the bone and an end section of the bone. The system includes an intramedullary core that is dimensioned for insertion in an intramedullary canal of the bone, and a hollow shell that is dimensioned for insertion in the intramedullary canal of the bone. The shell includes fixation elements that extend outwardly away from a proximal end of the shell. A fastener is provided for attaching the shell to the core in the intramedullary canal. When the core and shell are inserted in the intramedullary canal, the fixation elements extend away from the fracture line of the bone, and when the core and shell are attached in the intramedullary canal, the fixation elements engage an end surface of the end section of the bone. In one example version of the invention, the system is an olecranon fracture fixation system wherein the fixation elements are dimensioned to engage the triceps tendon and/or an end surface of the olecranon when the core and shell are attached in the intramedullary canal of the proximal ulna.

In one aspect of the fracture fixation system, one or more of the fixation elements can include a leg having a curved end that engages the end surface of the end section of the bone and/or the tissue.

In another aspect of the fracture fixation system, one or more of the fixation elements can include a wire loop having an outer end that engages an end surface of the end section of the bone and/or the tissue. The wire loop can include a coiled section defining a hole for receiving suture or other fastening device.

The fixation elements can extend axially and radially away from the proximal end of the shell, and at least two fixation elements can be on opposite sides of the shell.

In one form of the fracture fixation system, the intramedullary core includes a screw dimensioned to pass through a distal end of the shell. The fastener can transversely engage the screw, the shell and the bone for attaching the shell to the core in the intramedullary canal. The fastener can extend through an opening in the shell and an opening in the screw. The screw can include a first alignment guide and the shell can include a second alignment guide such that the rotational alignment of the screw and the shell can be controlled by aligning the first alignment guide and the second alignment guide. The shell can be dimensioned to extend distally beyond the fracture line when the fixation elements engage the end surface of the end section of the bone.

In another form of the fracture fixation system, the fastener engages a distal end of the shell and threadingly engages a proximal end of the core when attaching the shell to the core. A head of the fastener can engage the distal end of the shell. The fracture fixation system can further include a screw dimensioned for engaging the head of the fastener and at least one fixation element after the shell is attached to the core. The intramedullary core can include one or more longitudinal fins extending outward from a surface of the core.

The fracture fixation system can further include an insertion arm that engages the proximal end of the shell for insertion of the shell in the intramedullary canal of the bone. The insertion arm can engage the shell by way of threads on the insertion arm that engage threads on the shell. The insertion arm can include a drill guide for locating the fastener in the bone.

The fracture fixation system can further include a clamp for holding together the central section of the bone and the end section of the bone when the core and shell are inserted in the intramedullary canal.

These and other features, aspects, and advantages of the present invention will become better understood upon consideration of the following detailed description, drawings, and appended claims.

BRIEF DESCRIPTION OF THE DRAWINGS

FIG. 1 is a lateral view of an olecranon fracture fixation system according to the invention fixing an olecranon fracture with the ulna and olecranon being shown in cross-section.

FIG. 2 is an end view of the olecranon fracture fixation system of FIG. 1 taken along line 2-2 of FIG. 1.

FIG. 3 is a cross-sectional view of the olecranon fracture fixation system of FIGS. 1 and 2 taken along line 3-3 of FIG. 2.

FIG. 4 is a lateral view of an olecranon fracture fixation system of FIG. 1 being used with a drill guide according to the invention.

FIG. 5 is a lateral view of a second embodiment of an olecranon fracture fixation system according to the invention fixing an olecranon fracture with the ulna and olecranon being shown in cross-section.

FIG. 6 is an end view of the olecranon fracture fixation system of FIG. 5 taken along line 6-6 of FIG. 5.

Like reference numerals will be used to refer to like parts from Figure to Figure in the following description of the drawings.

DETAILED DESCRIPTION OF THE INVENTION

Looking first at FIGS. 1 to 4, there is shown one example embodiment of an olecranon fracture fixation system 10 according to the invention. The olecranon fracture fixation system 10 can be placed with an open technique or a minimally invasive percutaneous technique. The amount of fracture displacement will determine the need for open versus closed reduction.

With an open method, a temporary fracture holding clamp 12 may be used (see FIG. 1). The clamp 12 has a first pivoted leg 14 that is placed in the ulna 16 after being pre-drilled and a second pivoted leg 18 that engages the olecranon 20. The clamp 12 has locking ratchet teeth 22 that lock the clamp 12 and hold it. Two clamps can be utilized, one on the radial and ulnar borders of the ulna 16 and olecranon 20. This clamp 12 would not be used in the percutaneous closed reduction method.

The olecranon fracture fixation system 10 relies on a cannulation. Whether open or closed methods are utilized, a 0.062 Kischner wire (K wire) 24 is placed through the olecranon 20 across the fracture line 23 into the intramedullary canal 26 of the ulna 16. Care is taken to center the K wire 24 and fluoroscopic imaging can be utilized. Once the K wire 24 is placed in the intramedullary canal 26, a cannulated reamer is then placed over the K wire 24. There can be a soft-tissue protector and the intramedullary canal 26 can be reamed.

The olecranon fracture fixation system 10 of FIGS. 1 to 4 includes an outer hollow cylindrical shell 30 and an inner cylindrical intramedullary core 32. In one example form, the inner intramedullary core 32 is a 6.7 millimeter to 7.3 millimeter screw with threads 33. The inner intramedullary core 32 on the proximal end has a hexagonal recess screwdriver system 34. The center of hexagonal screwdriver system 34 has a cannulation hole 35 to be placed over the K wire 24. The inner intramedullary core 32 also has windows 36 that allow for 2.3 millimeter screws 38 to pass through the ulna 16 and windows 37 on the outer shell 30 to lock the shell 30 and the core 32. Laser alignment marks 40a on the end 42 the outer shell 30, and/or laser alignment marks 40b on the hexagonal screwdriver system 34 help make sure that the windows 36 cut out of the inner core 32 and the windows 37 of the outer shell 30 line up appropriately so that the screws 38 could easily pass.

The outer shell 30 proximally has threads 44 on its inside surface that allow engagement of an insertion arm 46. The insertion arm 46 has a hollow space 47 to be placed over the whole cannulated system so that the hexagonal screwdriver system 34 of the inner intramedullary core 32 can be utilized with a cannulated screwdriver 48 while maintaining the position of the shell 30 and the core 32. The insertion arm 46 inserts the outer shell 30 in the intramedullary canal 26, and the screwdriver 48 then advances and turns the core 32 in the shell 30. The insertion arm 46 has drill guides 49 distally that allow for drilling for one or two of the 2.3 mm screws 38. The insertion arm 46 is used whether it is an open or percutaneous technique. Again, the core 32 with its oval windows 36 should match up with the windows 37 on the outer shell 30 so that the screws 38 could pass through the shell 30 and core 32.

The olecranon fracture fixation system 10 includes a proximal fixation system having rigid legs 52 that come out from proximal end 42 of the outer shell 30. See FIGS. 2 and 3. The legs 52 grab the triceps tendon and olecranon fracture fragment to provide stabilization. These legs 52 can include three dorsally and three volarly, and then one both radially and ulnarly. Other numbers of legs 52 are also possible. These legs 52 have a radially outward curvature, which essentially come out of the drilled hole where the shell 30 has been placed and again, grab onto the tissue structures. The legs 52 can have teeth 54 on them that would help facilitate holding the soft tissue and olecranon. The use of a shell 30 with legs 52 minimizes the need for hardware removal. Currently, hardware removal is usually necessary with many fixation systems because of the discomfort experienced by patients of having an object between the olecranon and proximal ulna and the skin when they place any pressure on it. The olecranon fracture fixation system 10 would be locked and would be essentially within the bone and soft tissues, that it would not be palpable and would not require removal at a later date. Also, if the surgeon felt the need to go ahead and tension band, this option is still available for the surgeon to perform without compromising the olecranon fracture fixation system 10 in any fashion. Different types of legs 52 for the olecranon fracture fixation system 10 could be designed, i.e. in amount of bend, amount of lengths, amount of stiffness, and type of gripping surfaces. The leg technology on this olecranon fracture fixation system 10 may be applicable to other fracture types such as patella fractures, greater trochanteric fractures, and even potentially femur fractures.

Looking at FIGS. 5 and 6, there is shown another example embodiment of an olecranon fracture fixation system 60 according to the invention. The olecranon fracture fixation system 60 is a different intramedullary design, but for similar types of fractures. The olecranon fracture fixation system 60 includes a distal generally cylindrical intramedullary core 62. The intramedullary core 62 on the proximal end 63 has an internally threaded bore 64. Derotational outwardly extending longitudinal fins 66 on the intramedullary core 62 help prevent the core 62 from rotating in the intramedullary canal 26. The intramedullary core 62 also has windows 68 that allow for 2.3 millimeter locking screws 70 to pass through the ulna 16.

The olecranon fracture fixation system 60 also includes a hollow proximal shell 72 having loop wires 74 that come out from an outer proximal end 76 of the shell 72. The loop wires 74 are configured in almost a four-leaf clover pattern. See FIG. 6. Other numbers of loops are also possible. The loop wires 74 grab the triceps tendon and olecranon fracture fragment to provide stabilization. Derotational suture holes 77 formed by coiling a section of the wire of the loop wires 74 are also provided. The suture holes 77 allow the surgeon to weave suture through the suture holes and through the triceps tendon if needed. The use of a shell 72 with loop wires 74 minimizes the need for hardware removal. Currently, hardware removal is usually necessary with many fixation systems because of the discomfort experienced by patients of having an object between the olecranon and proximal ulna and the skin when they place any pressure on it. The olecranon fracture fixation system 60 would be locked and would be essentially within the bone and soft tissues, that it would not be palpable and would not require removal at a later date. Different types of loop wires 74 for the olecranon fracture fixation system 60 could be designed, i.e. in amount of bend, amount of lengths, amount of stiffness, and type of gripping surfaces. The loop wire technology on this olecranon fracture fixation system 60 may be applicable to other fracture types such as patella fractures, greater trochanteric fractures, and even potentially femur fractures. Also, the loop wires could be formed by a manufacturing process such as a mold technique, and then the suture holes 77 could be formed by machining through the metal.

The central part of the olecranon fracture fixation system 60 is a compression screw 78 that is inserted across the fracture line 23. This allows the surgeon to compress the fracture as needed. Threads 88 of the compression screw 78 engage the threaded bore 64 of the intramedullary core 62. The head 82 of the compression screw 78 engages an inwardly directed flange 83 of the distal end of the shell 72. An insertion arm device (similar to insertion arm 46) can be used to insert the shell 72 and place compression screw 78.

The olecranon fracture fixation system 60 also includes a first locking screw 84 and a second locking screw 89. The first locking screw 84 is inserted in the proximal to distal direction and passes through the shell 72 and the olecranon 20. The first locking screw 84 engages the head 82 of the compression screw 78 and a loop wire 74 after the shell 72 is attached to the core 62. The first locking screw 84 prevents the compression screw 78 from backing out. The second locking screw 89 is inserted in the distal to proximal direction and passes through the shell 72 and the olecranon 20.

The components of the olecranon fracture fixation system 10 and the olecranon fracture fixation system 60 may be formed from various materials such as, without limitation: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone).

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A fracture fixation system for a bone having a fracture line between a central section of the bone and an end section of the bone, the system comprising:
   an intramedullary core dimensioned for insertion in an intramedullary canal of the bone;
   a hollow shell dimensioned for insertion in the intramedullary canal of the bone, the shell including a plurality of fixation elements that extend outwardly away from a proximal end of the shell; and
   a fastener for attaching the shell to the core in the intramedullary canal,
   wherein the fixation elements extend away from the fracture line of the bone when the core and shell are inserted in the intramedullary canal, and
   wherein the fixation elements engage an end surface of the end section of the bone and/or tissue covering the end surface of the end section of the bone when the core and shell are attached in the intramedullary canal, and
   wherein the fixation elements extend axially and radially away from the proximal end of the shell, and
   wherein the fastener transversely engages the core and the shell, and the fastener is configured to directly contact the bone for attaching the core in the intramedullary canal, and wherein the proximal end of the shell does not extend proximally beyond the end surface of the end section of the bone when the core and shell are attached in the intramedullary canal.

2. The fracture fixation system of claim 1 wherein:
at least one of the fixation elements comprises a leg having a curved end that engages the end surface of the end section of the bone and/or the tissue.

3. The fracture fixation system of claim 1 wherein:
at least one of the fixation elements comprises a loop having an outer end that engages an end surface of the end section of the bone and/or the tissue.

4. The fracture fixation system of claim 1 wherein:
at least one of the fixation elements comprises a loop having an outer end that engages an end surface of the end section of the bone and/or the tissue, the loop including at least one section defining a hole.

5. The fracture fixation system of claim 1 wherein:
the bone is the ulna, and
the fixation elements are dimensioned to engage an end surface of the olecranon and/or tissue covering the end surface of the olecranon when the core and shell are attached in the intramedullary canal.

6. The fracture fixation system of claim 1 wherein:
at least two fixation elements are on opposite sides of the shell.

7. The fracture fixation system of claim 1 wherein:
the intramedullary core comprises a screw dimensioned to pass through a distal end of the shell.

8. The fracture fixation system of claim 7 wherein:
the fastener extends through an opening in the shell and an opening in the screw.

9. The fracture fixation system of claim 1 wherein:
the intramedullary core comprises a screw dimensioned to pass through the shell, and
the screw includes a first alignment guide and the shell includes a second alignment guide such that the rotational alignment of the screw and the shell can be controlled by aligning the first alignment guide and the second alignment guide.

10. The fracture fixation system of claim 1 wherein:
the intramedullary core comprises at least one longitudinal fin extending outward from a surface of the core.

11. The fracture fixation system of claim 1 wherein:
the shell is dimensioned to extend distally beyond the fracture line when the fixation elements engage the end surface of the end section of the bone.

12. The fracture fixation system of claim 1 further comprising:
an insertion arm that engages the proximal end of the shell for insertion of the shell in the intramedullary canal of the bone.

13. The fracture fixation system of claim 12 wherein:
the insertion arm engages the shell by way of threads on the insertion arm that engage threads on the shell.

14. The fracture fixation system of claim 12 wherein:
the insertion arm includes a drill guide for locating the fastener in the bone.

15. The fracture fixation system of claim 1 further comprising:
a second fastener engages a distal end of the shell and threadingly engages a proximal end of the core when attaching the shell to the core.

16. The fracture fixation system of claim 15 wherein:
a head of a second fastener engages the distal end of the shell.

17. The fracture fixation system of claim 15 further comprising:
a screw dimensioned for engaging the head of a second fastener and at least one fixation element after the shell is attached to the core.

18. A fracture fixation system for a bone having a fracture line between a central section of the bone and an end section of the bone, the system comprising:
an intramedullary core dimensioned for insertion in an intramedullary canal of the bone;
a hollow shell dimensioned for insertion in the intramedullary canal of the bone, the shell including a plurality of fixation elements that extend outwardly away from a proximal end of the shell; and
a fastener for attaching the shell to the core in the intramedullary canal,
wherein the fixation elements extend away from the fracture line of the bone when the core and shell are inserted in the intramedullary canal, and
wherein the fixation elements engage an end surface of the end section of the bone and/or tissue covering the end surface of the end section of the bone when the core and shell are attached in the intramedullary canal, and
wherein the fixation elements extend axially and radially away from the proximal end of the shell, and
wherein the system includes at least one fastener configured for attaching the core to the bone at a location on a side of the fracture line opposite the end section of the bone, and
wherein the core is configured such that portions of the core are located on both sides of the fracture line, and
wherein the proximal end of the shell does not extend proximally beyond the end surface of the end section of the bone when the core and shell are attached in the intramedullary canal.

19. The fracture fixation system of claim 1 wherein:
the shell includes three or more fixation elements.

* * * * *